United States Patent [19]

Hooper

[11] Patent Number: 4,472,436
[45] Date of Patent: Sep. 18, 1984

[54] INCREASING HDL-CHOLESTEROL LEVELS WITH PHENYLETHYLAMINE DERIVATIVES

[75] Inventor: Philip L. Hooper, Albuquerque, N. Mex.

[73] Assignee: Neo-Bionics, Inc., Albuquerque, N. Mex.

[21] Appl. No.: 447,125

[22] Filed: Dec. 6, 1982

[51] Int. Cl.³ .......................................... A61U 31/135
[52] U.S. Cl. .................................................. 424/330
[58] Field of Search ........................................ 424/330

Primary Examiner—Stanley J. Friedman
Attorney, Agent, or Firm—Herbert L. Gatewood

[57] ABSTRACT

High density lipoprotein (HDL) levels in serum cholesterol are increased by orally administering phenylethylamine derivatives having the structural formula

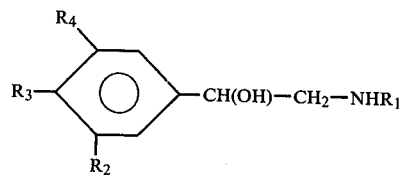

wherein $R_1$ is a member selected from the group consisting of —$CH(CH_3)_2$, —$C(CH_3)_3$ and

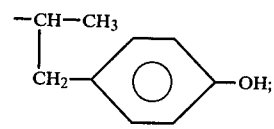

$R_2$ is a member selected from the group consisting of —OH and —$CH_2OH$; and $R_3$ and $R_4$, respectively, are members selected from the group consisting of —H and —OH.

8 Claims, No Drawings

INCREASING HDL-CHOLESTEROL LEVELS WITH PHENYLETHYLAMINE DERIVATIVES

BACKGROUND OF THE INVENTION (1) Field of the Invention

This invention relates to a method of increasing high density lipoprotein (HDL)-cholesterol levels in serum. In particular it relates to methods of increasing serum HDL-cholesterol levels by use of certain phenylethylamine derivatives.

(2) Description of the Prior Art

Coronary artery disease (CAD) in the United States accounts for 650,000 deaths annually at a cost of over $28.5 billion per year (American Heart Association Heart Facts. 1978, Dallas). It is the most common cause of death in this country. Over the years considerable research effort has been directed at finding factors which alter CAD risk. Factors associated with increased risk of CAD include smoking, hypertension, obesity, hyperlipidemia, inactivity, diet, being male, and genetic factors. On the other hand alcohol consumption, exercise, thinness, being female, and genetic predisposition are factors associated with decreased risk of CAD.

Much effort has been made to correct CAD risk factors including weight reduction, hypertension control, exercise, low cholesterol and saturated fat diet, smoking reduction, and lipid reducing agents. Lipid lowering products have been used in hyperlipoproteinemias in order to arrest, reverse, or prevent atherosclerosis. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyrozine, cholestyramine, and nicotinic acid [(Levy & Frederickson, Postgraduate Medicine 47, 130 (1970)].

Other useful hypolipidemic agents disclosed in the prior art and N,N'-disubstituted-p-phenylenediamines (U.S. Pat. No. 3,819,708) -αtertiary butyl-p-phenoxybenzlyamines (U.S. Pat. No. 3,946,119) and bis-substituted benzyl methanamines (U.S. Pat. No. 4,035,508).

If a drug could be found which increased HDL concentration, then ingestion of this substance might reduce the risk of CAD. Alcohol consumption has the above properties, however, its abuse potential and toxicity limit its practical usefulness.

High density lipoprotein (HDL)-cholesterol concentration has been found to be the best serum predictor of coronary artery disease (CAD). High levels of HDL are associated with a low risk of CAD and low levels with a high risk of CAD. High density lipoprotein appears to be the cholesterol "scavenger" of the body—it removes cholesterol from cells and carries it to the liver for excretion. Since factors which are associated with protection from coronary artery disease (exercise, alcohol consumption, estrogen, thinness, genetics) are associated with high HLD-cholesterol levels, it has been proposed that elevated serum HDL may bring about the protection. In fact, HDL has been called the "anti-atherogenic lipoprotein".

Recent reports have revealed that four Beta-adrenergic blockers (propranolol, metoprolol, atenolol, sotalol) lower HDL levels. Hooper, P. L.: Effect of Propranolol on Plasma Concentrations of HDL Apoproteins and Lipids. Br. Med. J. 6157:200, Jan. 1979; Bielmann, P. & Leduc, G.: Effects of Metoprolol and Propranolol on Lipid Metabolism. Int. J. Clin. Pharmacol Biopharm. 17:378-382, 1979. England, J. D. F.: et al. The Effect of Metoprolol and Atenolol on Plasma HDL Levels in Man. Clin. Exp. Pharmacol. Physiol. 7:329-33, 1980. Lehtonen, A.: Long-Term Effect of Sotalol on Plasma Lipids. Clin. Sci. 57:Suppl. 5:405$_s$-7$_s$, 1979.

SUMMARY OF THE INVENTION

I have now discovered that certain of the sympathomimetic amines, i.e., those which are Beta receptor stimulants, are capable of increasing HDL-cholesterol concentration. Those preferred are the Beta$_2$ receptor stimulants, as their presently known pharmacologic action is essentially on bronchi and not the heart. Thus, the amines found useful in the practice of this invention are derivatives of phenylethylamine represented by the following structural formula:

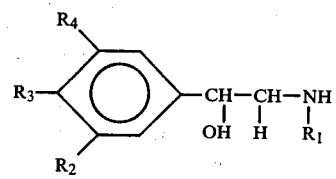

wherein $R_1$ is a member selected from the group consisting of $-CH(CH_3)_2$, $-C(CH_3)_3$ and

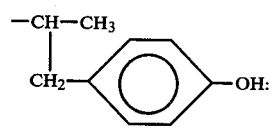

$R_2$ is a member selected from the group consisting of $-OH$ and $-CH_2OH$; $R_3$ and $R_4$ are members selected from the group consisting of $-H$ and $-OH$. Terbutaline, metaproterenol, fenoterol and salbutomal, all known beta$_2$ agonists, satisfy the above formula and will be found satisfactory in the practice of the invention.

BRIEF DESCRIPTION OF THE DRAWING

The sole FIGURE of the drawing shows two curves showing the effect on serum HDL-Cholesterol of the administration of terbutaline on two patients over a five week period.

DETAILED DESCRIPTION OF THE INVENTION

The phenylethylamine derivatives useful in the practice of this invention can be administered orally or parenterally, oral administration being preferred since patients usually will take these agents for a number of years. Various pharmaceutical prepartions can be made suitable for this purpose by following the conventional techniques of the pharmaceuticl chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as being very convenient in preparing formulations. The compositions may take the form of tablets, linguets, powders, capsules, slurries, troches or lozenges, and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize, starch or alginic acid, lubricating agents such as magnesium stearate and sweetening agents such as sucrose, lactose, or saccharin may be added, or a flavoring agent such as peppermint, oil of wintergreen, or cherry flavoring may be used. A preferable tablet composition is one which comprises from about 1 to about 10 milligrams of a compound of this invention.

If a liquid carrier is used, the preparation may be in the form of a soft gelatin capsule, a syrup, a liquid solution or suspension. A syrup or elixir may contain the active compound sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The hydrocarbon solubility of most of the compounds of this invention is high enough to allow the use of pharmaceutically-acceptable oils as carriers. For example, vegetable or animal oils such as sunflower oil, safflower oil, maize oil or codliver oil can be used. Glycerine can also be used. With this latter solvent, from 25 to 30 percent water may be used. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum asacia or gum tragacanth. Aqueous based suspensions may be prepared with the aid of wetting agents such as polyethylene oxide condensation products of alkylphenols, fatty alcohols or fatty acids and with suspending agents, for example a hydrophilic colloid such as polyvinylpyrrolidone. The emulsions and suspensions may contain conventional excipients such as sweetening agents, flowing agents, coloring materials and preservatives.

The compounds of this invention may be administered in the form of a nutritive preparation in which the active ingredient is mixed with protein, such as casein, and carbohydrates. In addition to the active ingredient, dietary supplements such as vitamins, salts of glycerophosphoric acid, choline, inositol and amino acids such as methionine may be added.

The percentage of the compound to be used in the pharmaceutical carrier may be varied. It is necessary that the compound constitute a proportion such that a suitable dosage will be obtained and it is preferred to use pharmaceutical compositions containing at least 0.5 weight percent of the compound. Activity increases with concentration of the agent in the carrier, but those compositions containing a significant amount of carrier, (98 to 99.5 percent carrier) are preferred as they allow for the easier administration of the compound.

For parenteral use, the compounds of this invention can be formulated with sterile ingredients, compounded and packaged aseptically. They may be administered intravenously or intramuscularly. Useful solvents for formulation in such use are the polyhydric aliphatic alcohols and mixtures thereof. Expecially satisfactory are the pharmaceutically acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly conveninet solvent system. A pH range, about 7.4, and isotonicity compatible with body isotonicity, is desirable. Basicity may be controlled by addition of a base as required, and a particularly conveninet base is monoethanolamine. It may often be desirable to incorporate a local anesthetic and such are well known to those skilled in the art. For example, lidocaine (p-di-ethylamine-2, 6-acetoxylidide, available from the Astra Chemical Co.), may be employed at a level of up to about 20 mg/cc., or even more.

It is not intended that the dosage regimens of the compounds be limited to any particular range. The dosage range desired in this invention is that range necessary to accomplish the desired end of increasing HDL-cholesterol, to the extent desired. The increase in HDL-cholesterol level desired will not be the same for all patients, but depends on such factors as initial HDL-cholesterol level, patient's sex, obesity, cigarette smoking, diet, predominance of one form of lipid over another, etc. The dosage, whether oral or parenteral, must, therefore, by necessity be individually determined by the physician. Likewise, the concentration range of the compounds in the various formulations of this invention is not limited. The concentration should be high enough to avoid an excessive number of administrations per day, but low enough to allow flexibility in administration.

Administration of the compounds of this invention by the oral route is preferred. Preferred daily dosages can be as low as 5 mg. Higher dosages can be given. Generally, one uses as a small a dose as will afford the desired response. This reduces chance of appearance of undesirable side effects. A convenient upper limit is about 18 milligrams per person per day. A preferred range of daily dosage is about 5 to 15 milligrams. In terms of body weight preferred dosages are from 0.05 to 0.3 mg. per kg. of body weight per day with a preferred range of about 0.1 to 0.25 mg. per kg. of body weight per day. The daily dosage is preferably administered from one to four or five times daily in amounts of from about 2.5 mg. to about 5.0 mg. and these amounts may be administered in dosage units containing at least 2.5 mg. of the compound. For example, when administering the compound in tablet form several tablets containing from, say 2.5 to 4 mg. of active compound can be administered up to 4 or more times daily. Alternatively, larger dosage units containing more of the compound, say 4 to 5 mg. can be administered at less frequent intervals.

For parenteral applications daily dosages of from about 5% to about 25% of the oral dosages are preferred. Thus daily dosages can be as low as 0.01 mg. to about 0.05 mg. per kg. body weight. The maximum dosage is determined only by physical limitations. A convenient upper limit is about 3 mg. From about 0.1 to about 0.3 mg. per injection (dosage unit in concentrations of about 0.5 to 1 mg./c.c., with from 2 to 5 injections of from 0.1 c.c. to 0.5 c.c. daily will give the required amount. Preferred formulations will contain from 0.5 to 1 mg./c.c. to be given in one injection of from 0.1 c.c. to 5 c.c.

Larger or smaller doses can be used and, in some cases, might be preferred in individual cases. Likewise administration need not be on a daily basis, although this is preferred, but may be, for example, on alternate days or even weekly and the like. With either oral or parenteral use, a daily regimen is preferred. However, even a single administration will have some effect.

Although the administration of the phenylethylamine derivatives has been more particularly disclosed earlier as being either orally or parenterally, it will be appreciated by those skilled in the art that these compounds can also be administered by either a metered dose inhaler or as an inhalant solution. In the case of a metered dose, the derivatives can be administered as is usual as a micronized powder in an inert propellant. Each metered dose expressed from the inhaler will deliver at the mouth piece the desired amount of compound for a unit dosage, as earlier disclosed. Where the phenylethylamine derivatives used in the practice of the invention are administered as an inhalant solution, the particular derivative will be supplied as a solution in an inert diluent such as saline solution commonly used for this purpose. Oral inhalation is administered with the aid, according to usual technique, of a hand bulb nebulizer or an intermittent positive pressure breathing apparatus. Various solutions can obviously be made up, e.g., a 5% solution in bottles of 10 ml. with accompanying calibrated dropper, but this will depend on a number of factors as earlier disclosed including the particular dosage requirements for a particular patient.

The active ingredient can be administered in the form of a salt, if desired. For example, terbutaline sulfate is commercially available in both tablet form and in ampules for subcutaneous injection from Astra Parmaceutical Products, Inc., Worcester, Massachusetts under the brand name BRICANYL.

The population that would benefit from a rise in HDL-cholesterol concentration is large since 40% of the United States population die of CAD. Subjects that are of particular risk for CAD are men, smokers, obese subjects, people with a family history of CAD, inactive subjects, and nonethanol consumers.

The invention will be better understood in conjunction with the following specific example.

METHODS

After giving informed consent, 15 healthy, nonobese men 23 to 45 years old with normal serum cholesterol levels were studied. The subjects were nonsmokers and nonjoggers, and they were asked not to alter habits known to alter lipid metabolism, such as alchohol ingestion and diet. After a base-line lipid profile was obtained during fasting, the 15 subjects received a 2.5 mg. BRICANYL ® terbutaline sulfate tablet (containing the equivalent of 2.05 mg. free base, white in color, NDC product code 725) orally four times a day for a two-week period. Two additional subjects received the terbutaline sulfate tablets at the same dose for a two-week period. Two additional subjects received the terbutaline sulfate tablets at the same dose for a five-week period. Fasting-state lipid values were determined weekly during terbutaline administration and again one week after the drug was stopped.

While subjects were fasting, serum was analysed for concentration of cholesterol (Levine, J. B. and Zak B.: Automated Determination of Serum Cholesterol. Clin Chim Acta. 10:381–4, 1964), triglyceride (Kessler G. and Lederer H.: Flourimetric Measurement of Triglycerides. In: Automation in Analytical Chemistry: Technician Symposia. White Plains, N.Y,: Mediad Inc., 341–4, 1965), and HDL cholesterol (Lopes-Virella M. F., Stone P., Ellis S., and Colwell, J., A. Cholesterol Determination in High Density Lipoprotein Separated By Three Different Methods. Clin Chem. 23:882–4, 1977). Lipid values corresponded with primary standards prepared by the Centers for Disease Control, Atlanta. Values for LDL cholesterol were calculated according to the procedure of Friedewald et al. Friedewald W. T., Levy, R. I., Fredrichson, D. S. Estimation of the Concentration of Low-Density Lipoprotein Cholesterol in Plasma, Without Use of The Preparative Ultracentrifuge, Clin. Chem. 18:499–502, 1972. Statistical analysis was conducted by two-factor analysis of variance, followed by the Newman-Keuls test. Zar J.H. Biostatistical Analysis. Englewood Cliffs, N. J.: Prentice-Hall, 170, 1974.

The table below shows that a rise in HDL-cholesterol concentration was associated with two weeks of terbutaline administration in 15 subjects. After one week of terbutaline administration, the HDL-cholesterol concentration had increased significantly ($P<0.005$). By the second week, HDL-cholesterol levels had risen 10 percent from the base-line value (from 40.8 to 44.9 mg. per deciliter [1.06 to 1.16 mmol per liter]; $P<0.005$). One week after terbutaline administration was stopped, HLD-cholesterol values returned to near the base-line values. Total cholesterol, triglyceride, and LDL-cholesterol levels did not change significantly throughout the study.

| Serum Lipid and Lipoprotein Levels in 15 Subjects Receiving Terbutaline* | | | | |
|---|---|---|---|---|
| Substance | Base Line | 1 week | 2 Weeks | 1 Week Off |
| Total cholesterol, (mg/dl) | 149.1 ± 17.1 | 146.3 ± 15.9 | 147.7 ± 13.0 | 150.2 ± 17.6 |
| Triglyceride, (mg/dl) | 109.3 ± 35.8 | 104.1 ± 29.4 | 105.2 ± 24.0 | 111.8 ± 36.5 |
| LDL-cholesterol, (mg/dl) | 86.4 ± 16.4 | 81.2 ± 17.6 | 83.3 ± 13.9 | 85.9 ± 17.1 |
| HDL-cholesterol, (mg/dl) | 40.8 ± 6.2 | 44.2 ± 7.2+ | 44.9 ± 6.6+ | 42.7 ± 7.0 |

*Values are expressed as means of 15 determination ±S.D. To convert cholesterol values to millimoles per liter, multiply by 0.02586. To convert triglyceride values to millimoles per liter, multiply by 0.01129.
+$P<0.005$ as compared with the base-line value.

Turning now to the figure of the drawing there is shown the effect of five weeks of terbutaline administration in two subjects. HDL-cholesterol levels rose to a maximum at two weeks and continued to be elevated throughout the period of terbutaline administration. HDL-cholesterol returned to base-line values one week after terbutaline administration was stopped.

The study demonstrates that the administration of terbutaline, a beta-adrenergic agonist, is associated with a significant rise in HDL-cholesterol values. The magnitude of the increase is comparable to that of the rise in HDL-cholesterol seen in men who have joined a cardiac rehabilitation program (Erkelens, D. W., et al. High-density Lipoprotein-Cholesterol in Survivors of Myocardial Infarction. JAJA 242:2185–9, 1979).

It should be understood that the specific embodiments described herein are merely exemplary of the preferred practice of the present invention and that various modifications and changes may be made in the

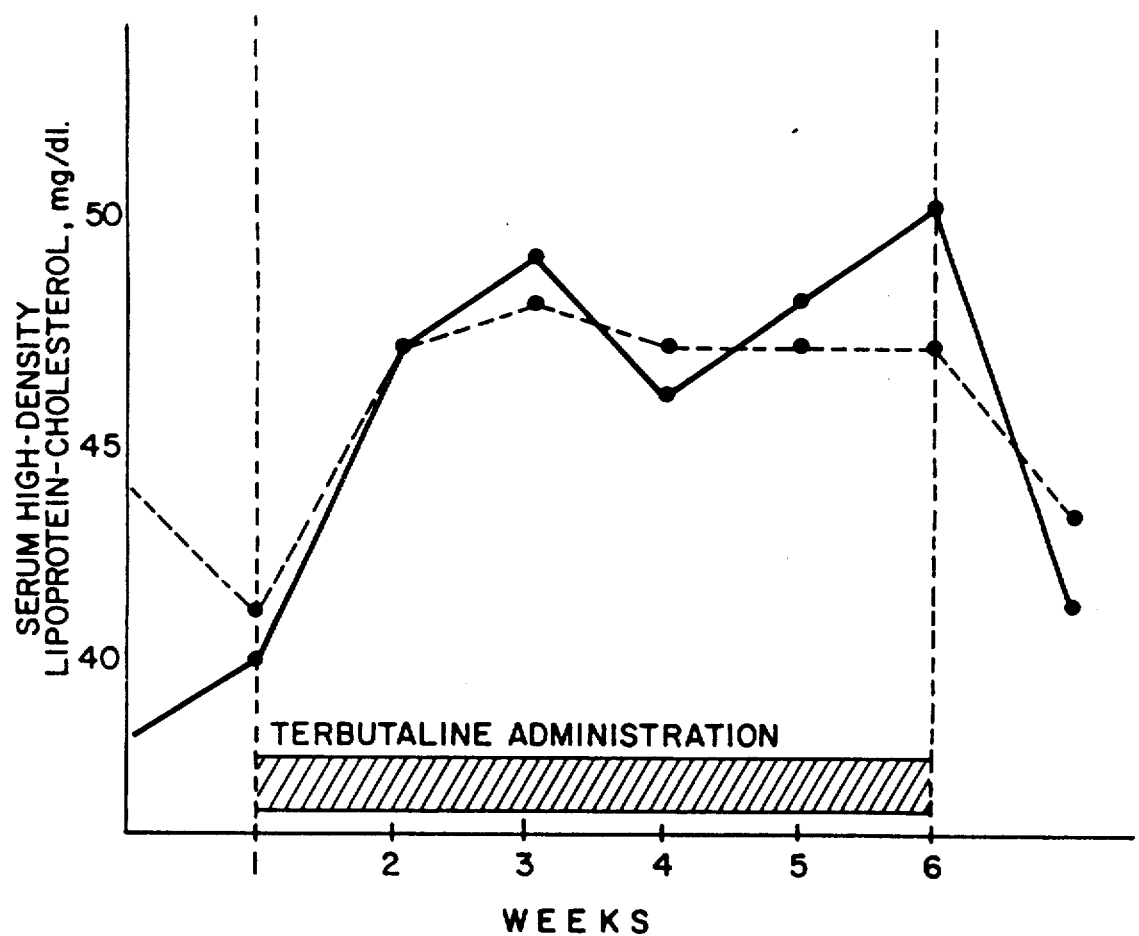

What I claim is:

1. The method of increasing the high-density-lipoprotein (HDL) cholesterol concentration in human serum in a host having a relatively high risk of coronary-artery disease without significantly changing the total cholesterol, triglyceride, and LDL-cholesterol levels, which method comprises administering to a human host an amount of terbutaline sufficient to increase the HDL concentration to the desired level above that host's base HDL level.

2. The method of increasing the high-density-lipoprotein (HDL) cholesterol concentration in human serum in a host having a relatively high risk of coronary-artery disease without significantly changing the total cholesterol, triglyceride, and LDL-cholesterol levels according to claim 1 wherein the terbutaline is administered orally and the daily dosage given is sufficient to obtain the desired HDL level.

3. The method of increasing the high-density-lipoprotein (HDL) cholesterol concentration in human serum in a host having a relatively high risk of coronary-artery disease without significantly changing the total cholesterol, triglyceride, and LDL-cholesterol levels according to claim 2 wherein the daily dosage is between 5 to 15 mgs.

4. The method of increasing the high-density-lipoprotein (HDL) cholesterol concentration in human serum in a host having a relatively high risk of coronary-artery disease without significantly changing the total cholesterol, triglyceride, and LDL-cholesterol levels according to claim 2 wherein the daily dosage is from 0.05 to 0.3 mg. per kg. of body weight.

5. The method of increasing the high-density-lipoprotein (HDL) cholesterol concentration in human serum in a host having a relatively high risk of coronary-artery disease without significantly changing the total cholesterol, triglyceride, and LDL-cholesterol levels according to claim 1 wherein the terbutaline is administered as terbutaline sulfate.

6. The method of increasing the high-density-lipoprotein (HDL) cholesterol concentration in human serum in a host having a relatively high risk of coronary-artery disease without significantly changing the total cholesterol, triglyceride, and LDL-cholesterol levels according to claim 5 wherein the terbutaline is administered as a 2.5 mg. terbutaline sulfate tablet containing 2.05 mg. free base.

7. The method of increasing the high-density-lipoprotein (HDL) cholesterol concentration in human serum in a host having a relatively high risk of coronary-artery disease without significantly changing the total cholesterol, triglyceride, and LDL-cholesterol levels according to claim 6 wherein such a terbutaline sulfate tablet is administered four times a day.

8. The method of increasing the high-density-lipoprotein (HDL) cholesterol concentration in human serum in a host having a relatively high risk of coronary-artery disease without significantly changing the total cholesterol, triglyceride, and LDL-cholesterol levels according to claim 1 wherein the terbutaline is administered parenterally in daily dosages of from about 0.01 mg. to about 0.05 mg. per kg. body weight.

* * * * *

UNITED STATES PATENT AND TRADEMARK OFFICE
CERTIFICATE OF CORRECTION

PATENT NO. : 4,472,436
DATED : September 18, 1984
INVENTOR(S) : Philip L. Hooper It is certified that error appears in the above-identified patent and that said Letters Patent are hereby corrected as shown below:

On the face of the patent, "No Drawings" should read - 1 Figure drawing -.
In column 1, line 40, the word "and" should read - are -; same page, line 41," - αtertiary" should read - ; α - tertiary -; same page, the paragraph set forth at lines 44 - 48 should be located instead between lines 62 - 63.
In column 2, line 4, the word "Physiol" should be in italics;

line 58, the word "pharmaceuticl" should read - pharmaceutical -.
In column 4, lines 10 - 11 and 14, the word "conveninet" should read - convenient -.

The sheet of drawing should appear as shown on the attached sheet.

Signed and Sealed this

Thirtieth Day of April 1985

[SEAL]

Attest:

DONALD J. QUIGG

Attesting Officer    Acting Commissioner of Patents and Trademarks